(12) United States Patent
Edwards et al.

(10) Patent No.: US 9,617,590 B2
(45) Date of Patent: Apr. 11, 2017

(54) DNA SAMPLE PREPARATION AND SEQUENCING

(71) Applicant: STC.UNM, Albuquerque, NM (US)

(72) Inventors: Jeremy Edwards, Albuquerque, NM (US); Payman Zarkesh-Ha, Albuquerque, NM (US); Steven R. J. Brueck, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 271 days.

(21) Appl. No.: 14/347,690

(22) PCT Filed: Sep. 28, 2012

(86) PCT No.: PCT/US2012/057821
§ 371 (c)(1),
(2) Date: Mar. 27, 2014

(87) PCT Pub. No.: WO2013/049504
PCT Pub. Date: Apr. 4, 2013

(65) Prior Publication Data
US 2014/0329712 A1    Nov. 6, 2014

Related U.S. Application Data

(60) Provisional application No. 61/542,013, filed on Sep. 30, 2011, provisional application No. 61/550,166, filed on Oct. 21, 2011.

(51) Int. Cl.
*C12Q 1/68* (2006.01)
*G01N 27/414* (2006.01)

(52) U.S. Cl.
CPC ......... *C12Q 1/6869* (2013.01); *C12Q 1/6806* (2013.01); *C12Q 1/6874* (2013.01); *G01N 27/414* (2013.01); *G01N 27/4145* (2013.01); *Y10T 436/143333* (2015.01)

(58) Field of Classification Search
None
See application file for complete search history.

(56) References Cited

U.S. PATENT DOCUMENTS

| | | | |
|---|---|---|---|
| 2008/0274904 A1* | 11/2008 | Gormley | C12Q 1/6869 506/1 |
| 2009/0018024 A1 | 1/2009 | Church et al. | |
| 2010/0120098 A1* | 5/2010 | Grunenwald | C12N 15/10 435/91.2 |
| 2011/0039304 A1 | 2/2011 | Church et al. | |
| 2012/0322666 A1* | 12/2012 | Pham | C12Q 1/6869 506/2 |
| 2013/0034880 A1* | 2/2013 | Oldham | C12Q 1/6853 435/91.5 |

FOREIGN PATENT DOCUMENTS

| | | |
|---|---|---|
| WO | WO 2005/003375 A2 | 1/2005 |
| WO | WO 2011-044437 A2 | 4/2011 |
| WO | WO 2013/049504 A1 | 4/2013 |

OTHER PUBLICATIONS

U.S. Appl. No. 61/542,013, filed Sep. 30, 2011, Zarkesh-Ha et al.
U.S. Appl. No. 61/550,166, filed Oct. 21, 2011, Zarkesh-Ha et al.
Adey et al. "Rapid, low-input, low-bias construction of shotgun fragment libraries by high-density in vitro transposition". 2010. *Genome Biology.* 11:R119. 17 pages.
Allen et al. "Single Virus Genomics: A New Tool for Virus Discovery". 2011. *PLoS One.* 6:e17722.
Alsmadi et al. "Haplotypes Encompassing the KIAA0392 and PSMAS6 Gene Cluster Confer a Genetic Link for Myocardial Infarction and Coronary Artery Disease" 2009. *Ann Hum Genet* 73:475-483.
Bentley et al. "Accurate whole human genome sequencing using reversible terminator chemistry" 2008. *Nature* 456:53-59.
Bergen et al. "Comparison of yield and genotyping performance of multiple displacement amplification and OmniPlex whole genome amplified DNA generated from multiple DNA sources". 2005. *Human Mutation.* 26:262-270.
Bergen et al. "Effects of DNA mass on multiple displacement whole genome amplification and genotyping performance". 2005. *BMC Biotechnol.* 5:24. 11 pages.
Bi et al. "Design and synthesis of a chemically cleavable fluorescent nucleotide, 3'-O-allyl-dGTP-PC-Bodipy-FL-510 as a reversible terminator for DNA sequencing by synthesis". 2006. *J Am Chem Soc* 128:2542-2543.
Browning et al. "Haplotype phasing: existing methods and new developments". 2011 *Nat. Rev. Genet.* 12:703-714.
Chaisson et al. "Short read fragment assembly of bacterial genomes" 2008. *Genome Research.* 18:324-330.
Chaisson et al. "De novo fragment assembly with short mate-paired reads: Does the read length matter?". 2009. *Genome Research.* 19:336-346.
The 1000 Genomes Project Consortium. "A map of human genome variation from population-scale sequencing". 2010 *Nature.* 467:1061-1073.

(Continued)

*Primary Examiner* — David Thomas
(74) *Attorney, Agent, or Firm* — Mueting, Raasch & Gebhardt, P.A.

(57) ABSTRACT

This disclosure describes, in one aspect, a method for preparing DNA molecule for sequencing. Generally, the method includes fragmenting the DNA molecule into double-stranded fragments; amplifying at least a portion of the double-stranded fragments; circularizing the fragments so that the first end of the fragment comprises a first loop connecting the strands and the second end of the fragment comprises a second loop connecting the strands; annealing a first sequencing primer to the first loop oriented to sequence at least a portion of one strand of the fragment; and annealing a second sequencing primer to the second loop oriented to sequence at least a portion of the other strand of the fragment. In another aspect, this disclosure describes a method for sequencing a DNA molecule. Generally, the method includes fragmenting the DNA molecule into double-stranded fragments; amplifying at least a portion of the double-stranded fragments; circularizing the fragments so that the first end of the fragment comprises a first loop connecting the strands and the second end of the fragment comprises a second loop connecting the strands; and sequencing at least one of the DNA strands.

27 Claims, 13 Drawing Sheets

(56) References Cited

OTHER PUBLICATIONS

Dapprich et al. "SNP-specific extraction of haplotype-resolved targeted genomic regions". 2008 *Nucleic Acids Research* 36(15):e94. 9 pages.
Denisov et al. "Consensus generation and variant detection by Celera Assembler". 2008. *Bioinformatics.* 24(8):1035-1040.
Eichler et al. "A haplotype map of the human genome" 2005. *Nature.* 437:1299-1320.
Eid et al. "Real-Time DNA Sequencing from Single Polymerase Molecules". 2009. *Science.* 323:133-138.
Flusberg et al. "Direct detection of DNA methylation during single-molecule, real-time sequencing". 2010. *Nature Methods.* 7:461-465.
Foster et al. "Whole genome amplification from filamentous fungi using Phi29-mediated multiple displacement amplification". 2005. *Fungal Genet. Biol.* 42:367-375.
Gonzalez et al. "Multiple displacement amplification as a pre-polymerase chain reaction (pre-PCR) to process difficult to amplify samples and low copy number sequences from natural environments". 2005. *Environ Microbiol.* 7:1024-1028.
Guo et al. "An integrated system for DNA sequencing by synthesis using novel nucleotide analogues". 2010. *Acc Chem Res* 43(4):551-563.
Guo et al. "Four-color DNA sequencing with 3'-O-modified nucleotide reversible terminators and chemically cleavable fluorescent dideoxynucleotides". 2008. *PNAS USA.* 105(27):9145-9150.
Imelfort et al. "De novo sequencing of plant genomes using second-generation technologies". 2009. *Briefings in bioinformatics.* 10:609-618.
Kitzman et al. "Haplotype-resolved genome sequencing of a Gujarati Indian individual". 2011. *Nature Biotechnology.* 29:59-63.
Korlach et al. "Chapter 20—Real-Time DNA Sequencing from Single Polymerase Molecules". 472:431-455. 2010.
Langmead. "Aligning short sequencing reads with Bowtie". 2010. *Curr. Protoc Bioinformatics.* Chapter 11, Unit 11.17. 24 pages.
Langmead et al. "Ultrafast and memory-efficient alignment of short DNA sequences to the human genome". 2009. *Genome Biology.* 10:R25. 10 pages.
Levy et al. "The Diploid Genome Sequence of an Individual Human". 2007. *PLoS Biology.* 5(10:5:e254. 32 pages.
Li et al. "Fast and accurate short read alignment with Burrows-Wheeler transform". 2009. *Bioinformatics.* 25(14):1754-1760.
Li et al. "Fast and accurate long-read alignment with Burrows-Wheeler transform" 2010. *Bioinformatics.* 26(5):589-595.
Lin et al. "Comparative studies of de novo assembly tools for next-generation sequencing technologies". 2011. *Bioinformatics.* 27(15):2031-2037.
MacDonald et al. "The Huntington's disease candidate region exhibits many different haplotypes". 1992. *Nature Genetics.* 1:99-103.
Marcy et al. "Nanoliter Reactors Improve Multiple Displacement Amplification of Genomes from Single Cells" 2007. *PLoS Genet.* 3(9):1702-1708.
McKernan et al. "Sequence and structural variation in a human genome uncovered by short-read, massively parallel ligation sequencing using two-base encoding". 2009. *Genome Res.* 19:1527-1541.
Nilsson et al. "Multiple Displacement Amplification of Isolated DNA from Human Gallstones: Molecular identification of Helicobacter DNA by Means of 16S rDNA-Based Pyrosequencing Analysis". 2005. *Helicobacter.* 10(6):592-600.
Rodrigue et al. "Whole Genome Amplification and De novo Assembly of Single Bacterial Cells". 2009. *PLoS ONE* 4:e6864.
Rothberg et al. "An Integrated Semiconductor Device enabling non-optical genome sequencing". 2011. *Nature.* 475(7356):348-352.
Ruffalo et al. "Comparative analysis of algorithms for next-generation sequencing read alignment". 2011. *Bioinformatics* 27:2790-2796.
Schadt et al. "Computational solutions to large-scale data management and analysis". 2010. *Nature Reviews Genetics.* 11:647-657.
Schadt et al. "A window into third-generation sequencing". 2010. *Human Molecular Genetics.* 19:R227-240.
Shearer et al. "Comprehensive genetic testing for hereditary hearing loss using massively parallel sequencing". 2010. *PNAS USA.* 107(49):21104-21109).
Tewhey et al. "The importance of phase information of human genomics". 2011. *Nat. Rev. Genet.* 12:215-223.
Yu et al. "Postal cloning of the Werner's syndrome gene". 1996. *Science.* 272(5259):258-262.
Zhang et al. "A Practical Comparison of De Novo Genome Assembly Software Tools for Next-Generation sequencing Technologies". 2011. *PLoS ONE* 6:e17915.
International Search Report. Issued on Feb. 14, 2013, by the Korean Intellectual Property Office for PCT/US2012/057821. 7 pages.
Written Opinion of the International Searching Authority. Issued on Feb. 14, 2013, by the Korean Intellectual Property Office for PCT/US2012/057821 . 5 pages.
International Preliminary Report on Patentability. International Application No. PCT/US2012/057821. Issued on Apr. 10, 2014. 2 pages.

\* cited by examiner

FIG. 14
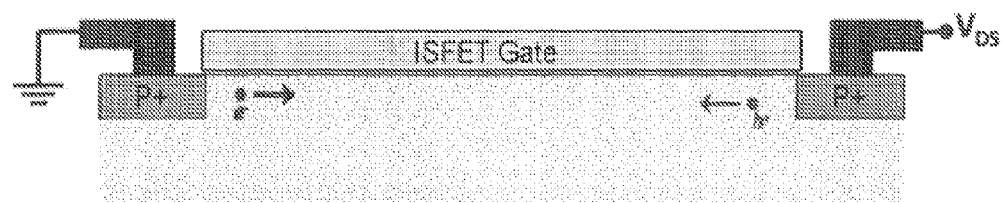
ISFET Normal Operation
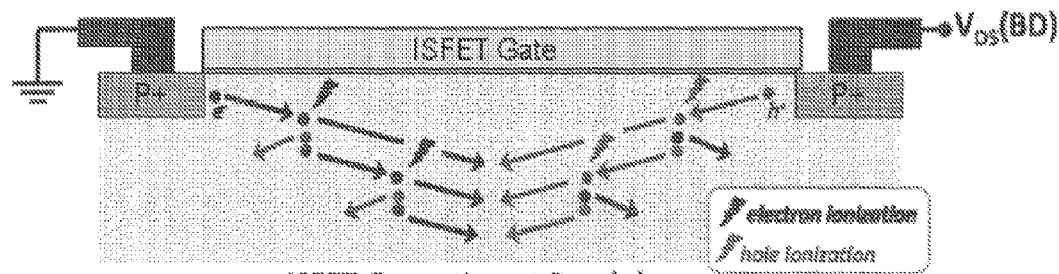
ISFET Operation at Breakdown

DNA SAMPLE PREPARATION AND SEQUENCING

CROSS-REFERENCE TO RELATED APPLICATION

This application is the §371 U.S. National Stage of International Application No. PCT/US2012/057821, filed 28 Sep. 2012, which claims priority to U.S. Provisional Patent Application Ser. No. 61/542,013, filed Sep. 30, 2011, and U.S. Provisional Patent Application Ser. No. 61/,550,166 filed Oct. 21, 2011, each of which is incorporated by reference herein in its entirety.

GOVERNMENT FUNDING

The present invention was made with government support under Grant No. R01 HG005852, awarded by the National Institutes of Health (NIH), and R01 HG006876, awarded by the National Institutes of Health (NIH). The government has certain rights in the invention.

SEQUENCE LISTING

This application contains a Sequence Listing electronically submitted via EFS-Web to the United States Patent and Trademark Office as an ASCII text filed entitled "U.S.14-347690 _SequenceListing_ST25.txt" having a size of 3 kilobytes and created on Jun. 11, 2014. The information contained in the Sequence Listing is incorporated by reference herein.

SUMMARY

This disclosure describes, in one aspect, a method for preparing DNA molecule for sequencing. Generally, the method includes fragmenting the DNA molecule into double-stranded fragments; amplifying at least a portion of the double-stranded fragments; circularizing the fragments so that the first end of the fragment comprises a first loop connecting the strands and the second end of the fragment comprises a second loop connecting the strands; annealing a first sequencing primer to the first loop oriented to sequence at least a portion of one strand of the fragment; and annealing a second sequencing primer to the second loop oriented to sequence at least a portion of the other strand of the fragment.

In another aspect, this disclosure describes a method for sequencing a DNA molecule. Generally, the method includes fragmenting the DNA molecule into double-stranded fragments; amplifying at least a portion of the double-stranded fragments; circularizing the fragments so that the first end of the fragment comprises a first loop connecting the strands and the second end of the fragment comprises a second loop connecting the strands; and sequencing at least one of the DNA strands.

In some embodiments of either aspect, the method can further include preparing an emulsion comprising a plurality of droplets that contain the circularized DNA fragments.

In some embodiments of either aspect, the DNA fragment is amplified prior to being circularized.

In some embodiments of either aspect, the method can further include immobilizing the circularized DNA fragments to a substrate. In some of these embodiments, the substrate can include a multi-well array. In other embodiments, the substrate can include a DG-ISFET device.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 14. Schematic of the avalanche buildup showing the cascade of impact ionizations in the channel region of an ISFET. The impact ionization drastically multiplies the number of free carriers generated by the gate, which in turn significantly increases the ISFET sensitivity.

DETAILED DESCRIPTION OF ILLUSTRATIVE EMBODIMENTS

Figure 1:
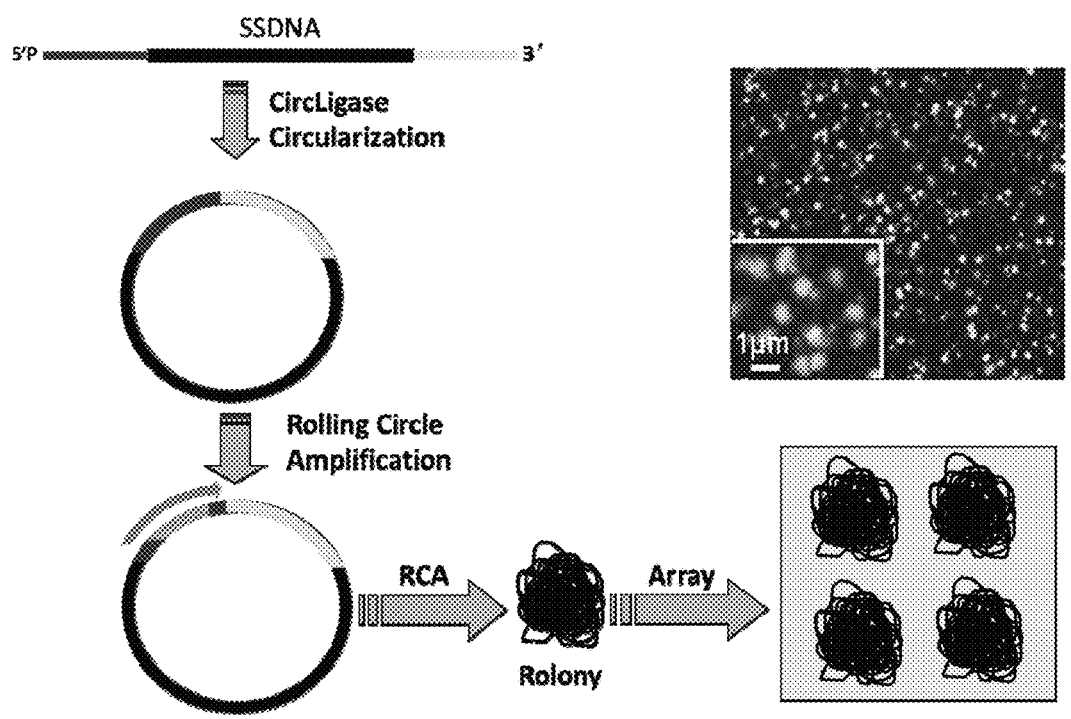
FIG. 1. Rolony formation. Rolling circle amplification of circularized fragment libraries leads to the formation of Rolonies (clumps of DNA) that can be arrayed and sequenced.
Figure 2:
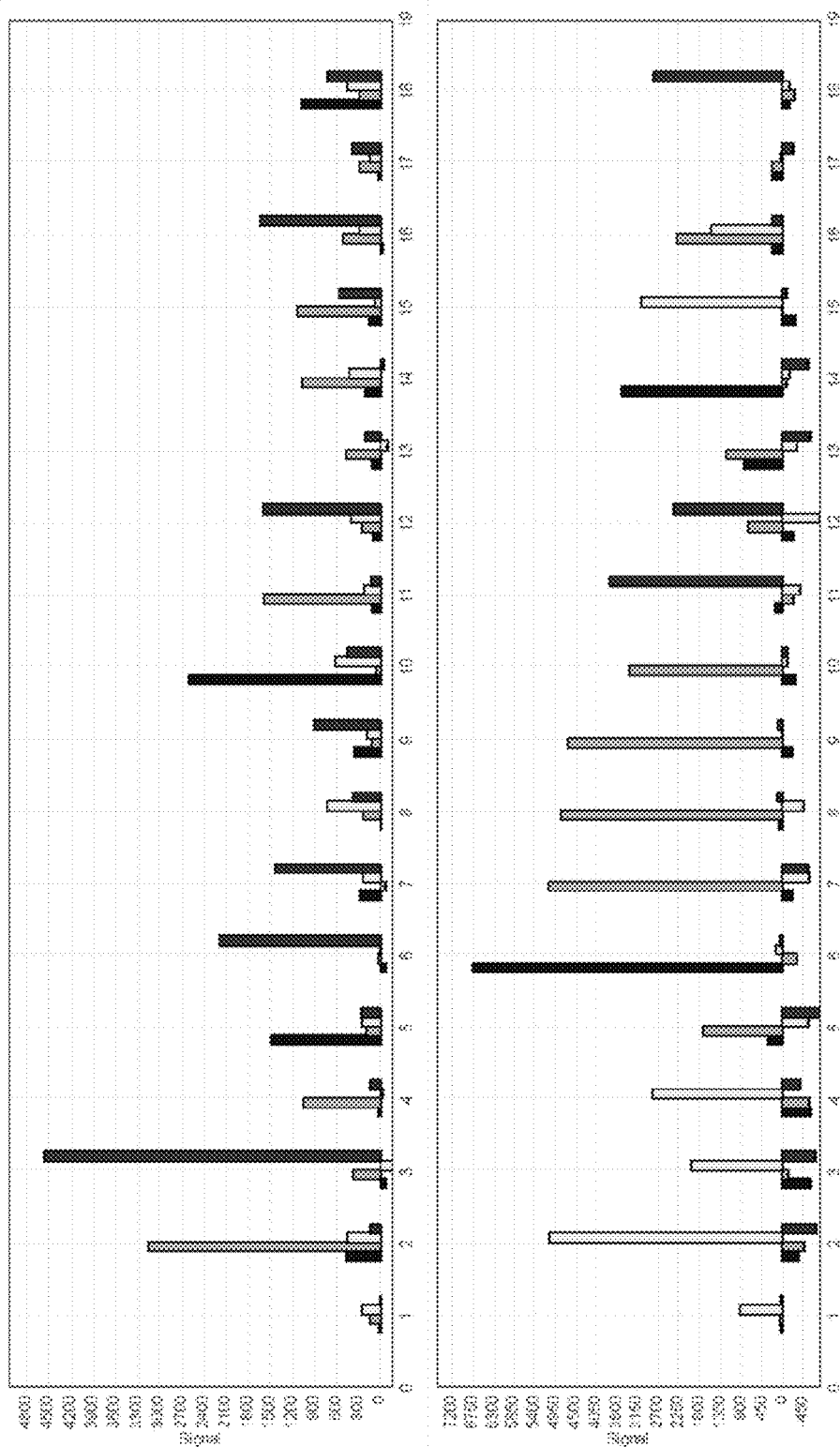
FIG. 2. Base calls from two separate rolonies (top and bottom). This is for an 18 base read cycle.

The success of the Human Genome Project (HGP) illustrates how early investments in developing cost-effective DNA sequencing methods can have tremendous payoffs for the biomedical community. Over the course of a little more than a decade, the HGP motivated a substantial reduction of sequencing costs, from $10 per finished base to less than $0.00001 per finished base. Once, the relevance and utility of sequencing and sequencing centers in the wake of the HGP was debated. Now, however, there is increasing demand for rapid and inexpensive sequencing.

One challenge in developing rapid, inexpensive, and accurate sequencing schemes is the diploid nature of the human genome: 23 pairs of chromosomes. Thus, each individual possesses two alleles for each genomic locus other than loci on the X or Y chromosomes. As a result, it may be insufficient to know that a person possesses a particular polymorphism such as, for example, a polymorphism associated with a particular disease or condition. Rather, one may want to know the extent to which a particular polymorphism is linked—i.e., located on the same chromosome—as another polymorphism. To obtain this information, one must be able to resolve the haplotype of the individual.

We describe herein novel and reliable tools that can economically and rapidly re-sequence a haplotype resolved human genome. A haplotype resolved human genome sequence assigns all polymorphisms to a specific chromosome. In other words, the cis or trans relation of all polymorphisms will be identified.

High-throughput DNA sequencing technologies have succeeded by spatially and temporally increasing the amount of information that can be gathered by, for example, miniaturization and/or increasing the speed of sample processing. Many ultra-high-throughput sequencing technologies exist (e.g., Illumina/Solex (Bentley et al. 2008 *Nature* 456:53-59), SOLiD (McKeman et al. 2009 *Genome Res* 19:1527-1541; Shearer et al. 2010 *Proc Natl Acad Sci USA* 107:21104-21109), Roche/454 (Margulies et al. 2005 *Nature* 437:376-380), Pacbio (Flusberg et al. 2010 *Nature methods* 7:461-465; Korlach et al. 2010 *Methods in enzymology* 472:431-455; Schadt et al. 2010 *Nature reviews. Genetics* 11:647-657; Schadt et al. 2010 *Human molecular genetics* 19:R227-240; Eid et al. 2009 *Science* 323:133-138; Imelfort and Edwards, 2009 *Briefings in bioinformatics* 10:609-618), Ion Torrent (Rothberg et al. 2011 *Nature* 475:348-352)) and more are under development. For example, polony technology utilizes only a single step to generate billions of "distinct clones" for sequencing and has led to a paradigm shift in DNA sequencing technology. The platform described herein can extend polony technology by, for example, creating higher density sequencing features (e.g., by using rolony technology) and increasing the speed of sequencing (e.g., non-light based sequencing strategy). As another example, ion-sensitive field-effect transistor (ISFET) sequencing technology provides a non-optically based sequencing technique. Our platform can increase the number of transistors by as much as an order of magnitude. The platform described herein may allow one to re-sequence a human genome in less than one day for less than $100 in reagent and labor costs.

Our platform methods may complement these and other sequencing methods by offering one or more the following features. Our platform can increase the speed at which the genome may be sequenced because it is non-light based sequencing. Unlike many other Sequencing-by-Synthesis (SBS) approaches, our approach is based on a standard DNA polymerase and unmodified dNTPs. The reagent costs of our platform are minimized because all reagents are standard. When used in conjunction with certain semiconductor chips (e.g., those described in more detail, below), one may be able to sequence more than 100 Gbases of per hour. Using rolony technology, we will be able to generate sub-micron sequencing features (e.g., 400 nm rolonies) that are much smaller than, and consequently allow greater transistor density than, other chip-based sequencing methods. The use of rolonies also can simplify library preparation and/or processes upstream of sequencing. The use of paired-end reads, which provides reads from both ends of a DNA fragment so that the relative spatial organization of the two reads is known, can simplify and/or improve post-sequencing analysis. Finally, our platform allows one to completely resolve haplotype even with short sequencing reads.

Recent advances in next generation sequencing technologies, along with the development of robust analysis methods, offer the ability to determine the role of sequence variations in human diseases. However, many of the approaches produce results that are limited to only finding polymorphisms, neglecting the importance of haplotypes (Browning and Browning, 2011 *Nat Rev Genet* 12:703-714). In contrast, haplotype resolved sequencing methods can determine the specific chromosome of each polymorphism. This is information may be useful because identifying the haplotype in which a polymorphism is detected can assist medical professionals in identifying disease-causing loci and in disease association studies (Kitzman et al. 2011 *Nature Biotechnology* 29:59-63; Consortium, 2010 *Nature* 467:1061-1073; Levy et al. 2007 *PLoS biology* 5:e254; Eichler et al. 2005 *Nature* 437:1299-1320; MacDonald et al. 1992 *Nature genetics* 1:99-103; Yu et al. 1996 *Science* 272:258-262; Tewhey et al. 2011 *Nat Rev Genet* 12:215-223; Alsmadi et al. 2009 *Ann Hum Genet* 73:475-483).

Today, commonly studied polymorphisms include single-nucleotide polymorphisms (SNPs) and other indels. Conventional next generation sequencing methods, while proficient in identifying heterozygous loci, can be inefficient in identifying cis or trans polymorphisms, thus complicating the search for associations between particular coding regions of the genome and particular diseases or conditions. Haplotypes are defined as a set of SNPs (and other polymorphisms) that are associated with one another. As a result, each individual has two haplotypes for a region of the genome (i.e., the maternal chromosome and the paternal chromosome). Therefore, despite having identical genotypes, two individuals may exhibit phenotypic differences that can manifest as disease diversity.

The lack of haplotype information obtainable from conventional existing sequencing approached contributes to difficulty drawing biological and medical conclusions from the sequencing information that is generated. For example, a list of polymorphisms classified merely as homozygous or heterozygous neglects the importance of the context of the polymorphism. One feature of haplotype resolved whole genome sequencing (hrWGS) over standard whole genome sequencing is that in hrWGS all polymorphisms are assigned to a specific chromosome. Haplotype resolved sequencing provides context of the polymorphism by defining the polymorphisms that exist together. This information can be valuable for exploiting genome sequencing information to identify associations between genetic variations and disease. To identify haplotypes and enable powerful genome association studies, simply increasing sequence coverage with existing short read technologies is insufficient for haplotype resolved sequencing. Despite the power of haplotypes for identifying gene-disease associations, the current next generation sequencing instruments are unable to identify haplotypes.

Figure 7:
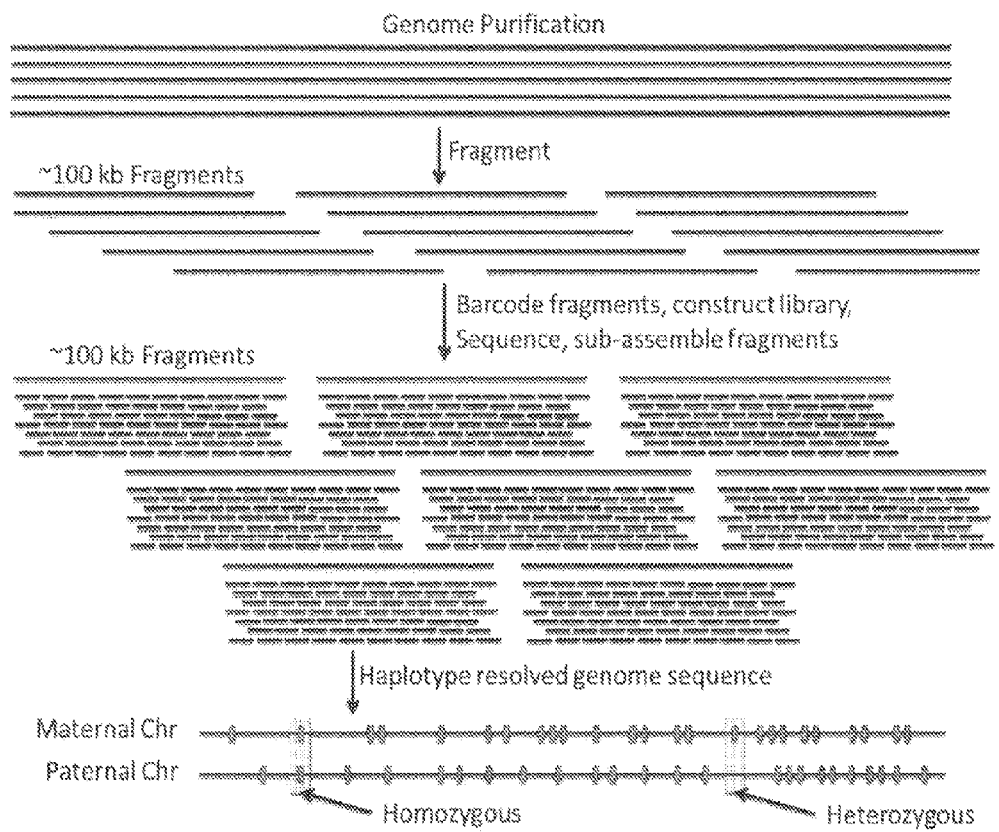
FIG. 7. Haplotype resolved genome subassembly. Large genomic DNA can be isolated and purified with ~100 kb to 200 kb size distribution. Individual libraries for each of the large fragments can be constructed. The libraries can be barcoded so when the short reads are obtained, the original 100 kb to 200 kb fragment can be identified. Finally, the large 100 kb to 200 kb fragments can then be assembled to generate the haplotype resolved human genome.

The general strategy for obtaining haplotype resolved whole genome sequencing (hrWGS) is shown schematically in FIG. 7. The process begins with isolating genomic DNA, which will naturally fragment into large fragments (100 kb-200 kb) when isolated using conventional methods such as, for example, a Qiagen kit (Puregene Blood Core Kit A). One can then construct a separate barcoded library for each of the 100 kb-200 kb fragments. The samples are then pooled and sequenced. The presence of the barcodes allow one to separate the data post-sequencing and assemble each 100 kb-200 kb fragment independently. The 100 kb-200 kb fragments can be assembled by any suitable analysis including, for example, de novo assembly (Levy et al. 2007 *PLoS biology* 5:e254; Zhang et al. 2011 *PLoS ONE* 6:e17915; Chaisson et al. 2009 *Genome research* 19:336-346; Lin et al. 2011 *Bioinformatics* 27:2031-2037; Denisov et al. 2008 *Bioinformatics* 24:1035-1040) or using read mapping (Ruffalo et al. 2011 *Bioinformatics* 27:2790-2796; Langmead, "Aligning short sequencing reads with Bowtie," in *Curr Protoc Bioinformatics* Chapter 11, Unit 11.17, 2010; Langmead et al. 2009 *Genome biology* 10:R25; Li and Durbin, 2010 *Bioinformatics* 26:589-595; Li and Durbin, 2009 *Bioinformatics* 25:1754-1760). The assembled 100 kb-200 kb fragments can then be assembled into a complete haplotype resolved genome sequence (FIG. 7).

Figure 8:
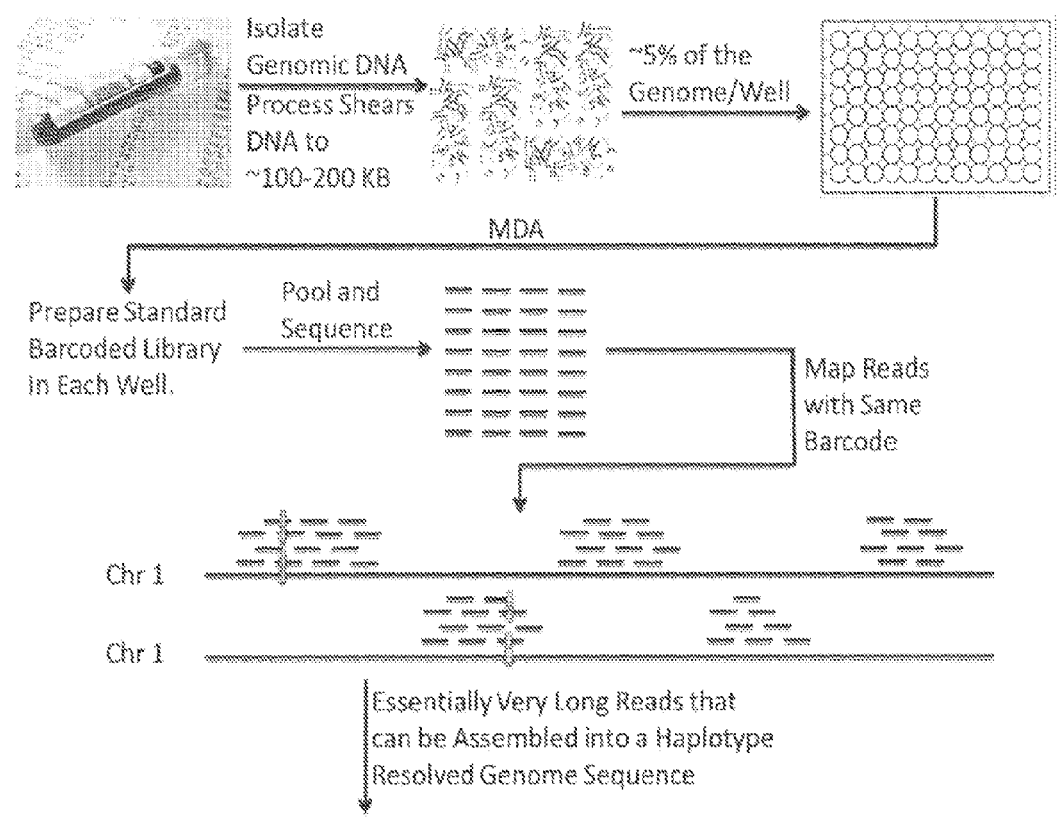
FIG. 8. Haplotype resolved sequence using 96-well plate and barcoding. In the final step, the mapped reads could also be de novo assembled. However, the de novo assembly will be most effective in the case when each well contains a single genome fragment, which is described in the following section using an emulsion-based library prep.

In some embodiments, shown schematically in FIG. 8, one can place a random ~10% of a fragmented genome (in 100 kb-200 kb fragments) in each well of a 96-well plate. One can amplify the DNA in each well—such as is shown in FIG. 6A—and construct a barcoded library for each well in the plate separately. The DNA is sufficiently diluted in each well so that two fragments in an individual well will not have come from the same region of the genome. All DNA from a single well are given the same barcode. All of the libraries will be constructed in the 96-well plate and then pooled and sequenced. If reads with the same barcode—i.e., from the same well—map to the same region of the genome, the reads will have come from the same 100 kb-200 kb fragment. One can generate sufficient raw sequencing data to completely sequence the DNA within each well. Therefore, one can have 10× genome coverage over all 96 wells, and one can assemble the 100 kb-200 kb fragments into a complete haplotype resolved genome.

Figure 9:
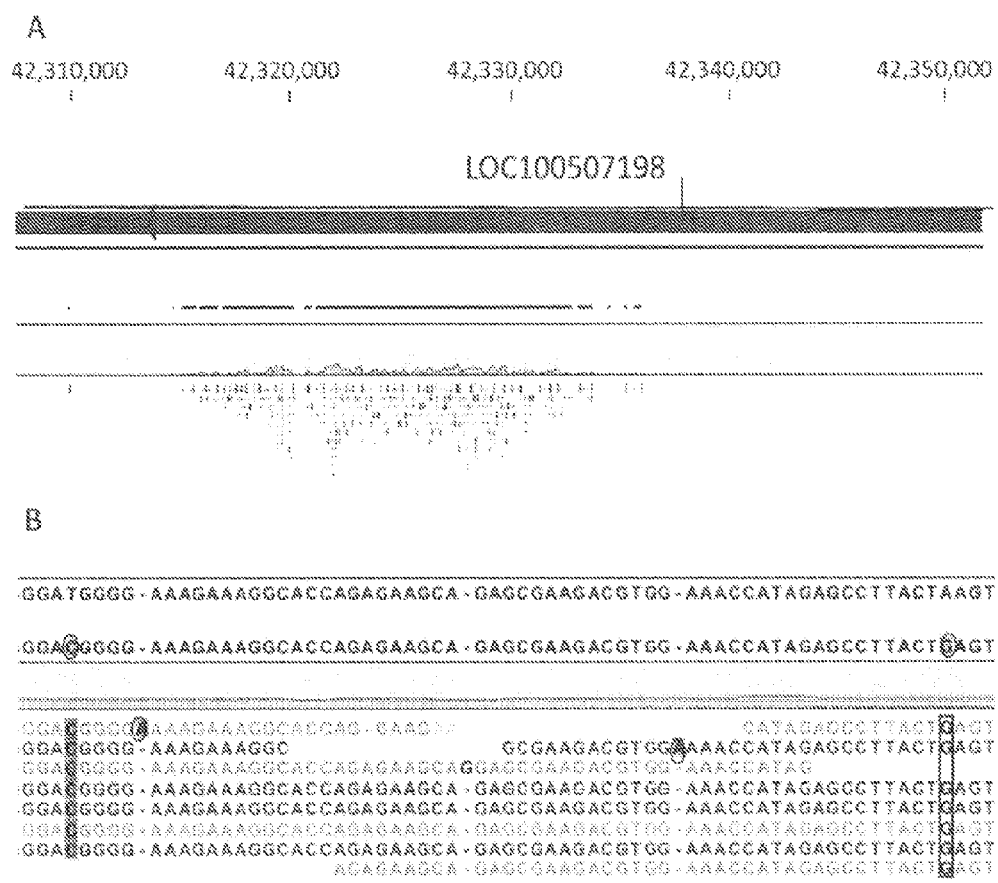
FIG. 9. Distribution of reads mapped to the human genome. A) Large number of reads mapped to approximately 12 kb region of the genome. B) SEQ ID NOs:1-10 (shown from top to bottom, respectively) show two homozygous SNP's (highlighted [C] and boxed [G]) identified in the same region. No heterozygous SNPs were identified anywhere, which indicates that single molecules derived from a single chromosome were used to construct the library.
Figure 13:
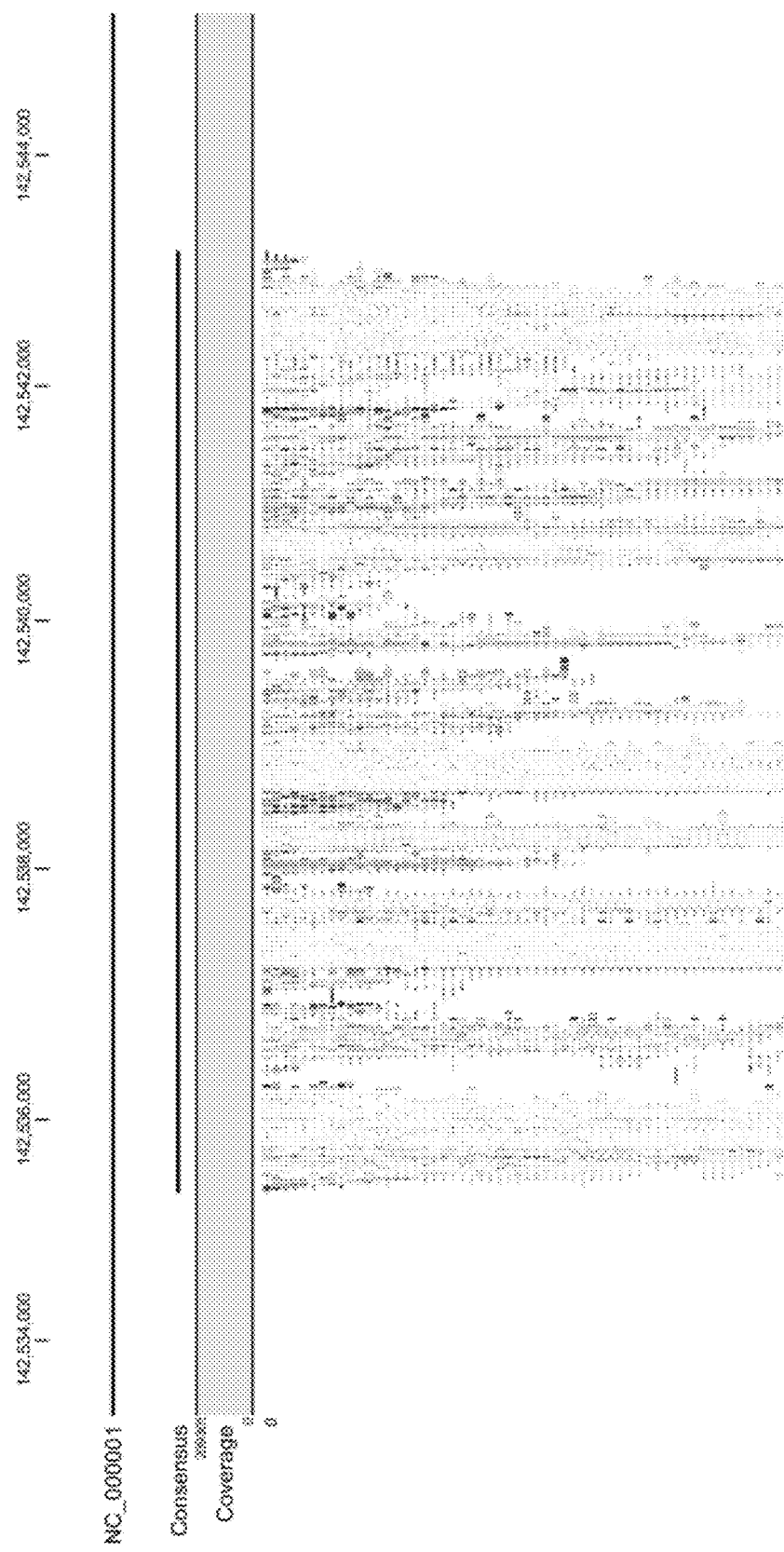
FIG. 13. Distribution of reads mapped to the human genome. Large number of reads mapped to approximately 8 kb region of the genome.

Preliminary data from a single well that was sequenced using the Ion Torrent (Ion Torrent Systems, Inc., South San Francisco, Calif.) platform is shown in FIG. 9. Here, the reads concentrated in specific regions of the genome (FIG. 9A). The preliminary data of FIG. 9 cover approximately 10% of the genome, as if all of the reads have come from a single chromosome. This is supported by the fact that all SNPs identified are homozygous (FIG. 9B). More complete data are presented in FIG. 13, showing a larger number of reads mapped to approximately 8 kb of the genome.

Thus, the 96-well plate approach is very powerful and can generate haplotype resolved genome sequencing. In some cases, one may desire to further dilute the genome. One can accomplish this by, for example, filtering data when heterozygous polymorphisms are identified or, perhaps, more simply, by using a 384-well plate. The 96-well plate approach requires constructing 96 libraries. Library construction may be, for example, automated and/or involve using an emulsion based library preparation for hrWGS.

Figure 10:
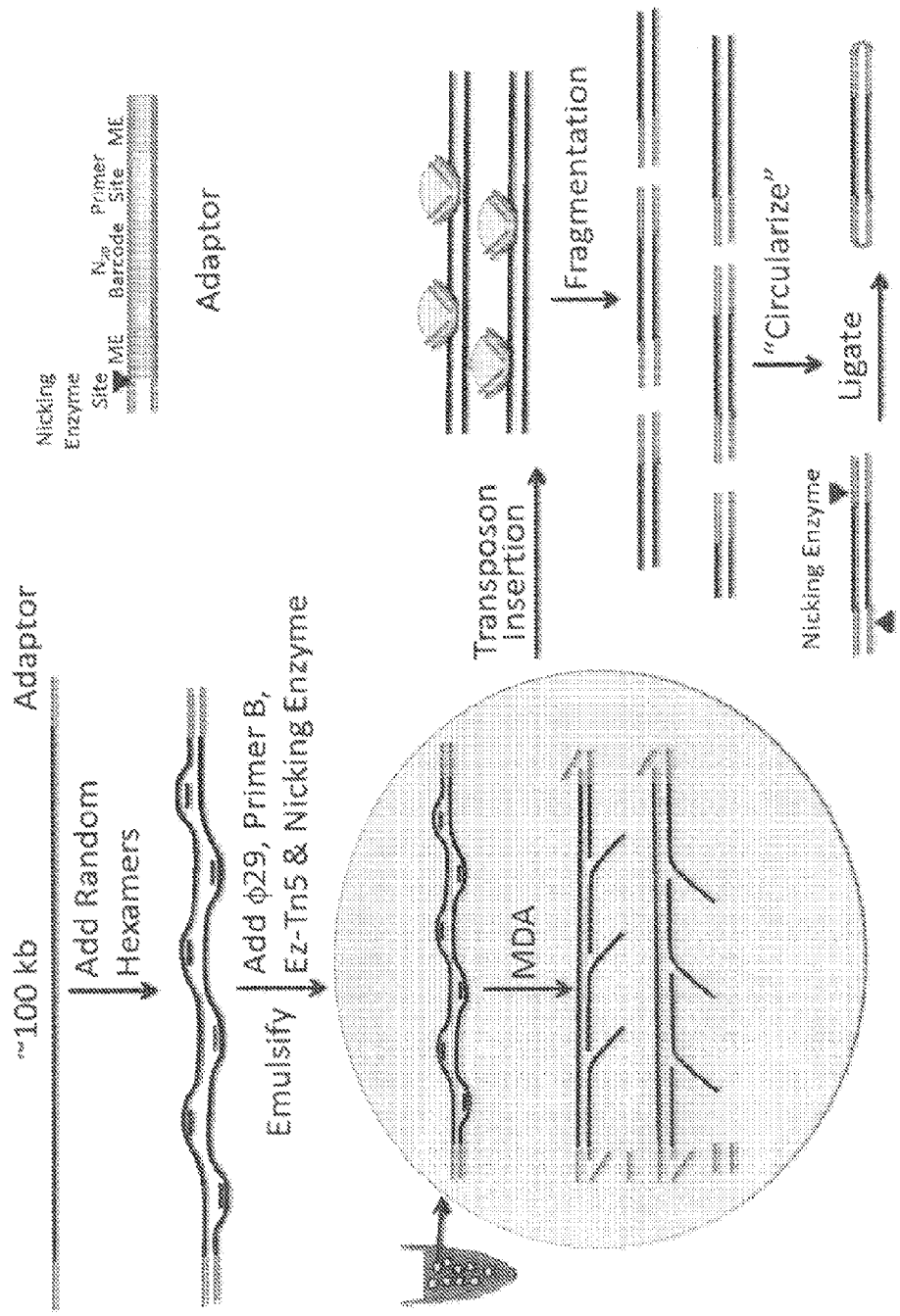
FIG. 10. Two alternate methods for generating libraries for haplotype resolved sequencing. Emulsions may be used to construct the libraries to allow each individual ~100-200 kb fragment to be contained in an individual compartment. The entire process of amplification and library construction can be carried out within a droplet. If needed, one can introduce the Tn5 transposase following amplification by merging droplets of opposite charge.

The 96-well plate library construction described above can be extended to millions of "wells," where each well has one or zero library molecules, by using emulsion droplets, illustrated schematically in FIG. 10. The barcode can be, for example, a random 20 mer oligo. The barcodes can be ligated to the genome fragments before the emulsion is formed so that when the fragments are loaded into the emulsion, the barcode will be present. A multiple displacement amplification (MDA) can be performed in the standard manner (Rodrigue et al. 2009 *PLoS ONE* 4:e6864; Bergen et al. 2005 *Hum Mutat* 26:262-270; Bergen et al. 2005 *BMC Biotechnol* 5:24; Foster and Monahan, 2005 *Fungal Genet Biol* 42:367-375; Gonzalez et al. 2005 *Environ Microbiol* 7:1024-1028; Marcy et al. 2007 *PLoS Genet* 3:1702-1708; Nilsson et al. 2005 *Helicobacter* 10:592-600; Allen et al. 2011 *PLoS ONE* 6:e17722), thus amplifying the single large fragment. The barcode is amplified at the same time as the genomic fragment by including a nicking enzyme in the mix that creates a nick, which is then recognized and subsequently amplified into ssDNA by, for example, φ29 enzyme (FIG. 10B). A reverse primer also can be included to convert the barcode into a dsDNA fragment that can be recognized by Tn5 for insertion into the amplified DNA, thus fragmenting the amplified genomic DNA loaded in the droplet.

Our haplotype resolved sequencing platform is based on an innovative library preparation approach, which involves novel high throughput library construction that maintains the simplicity of the existing library construction approaches. In certain embodiments, our platform exploits certain features of rolony technology, paired-end read technology, and/or high density ion-sensitive field-effect transistor (ISFET) technology.

Figure 5:
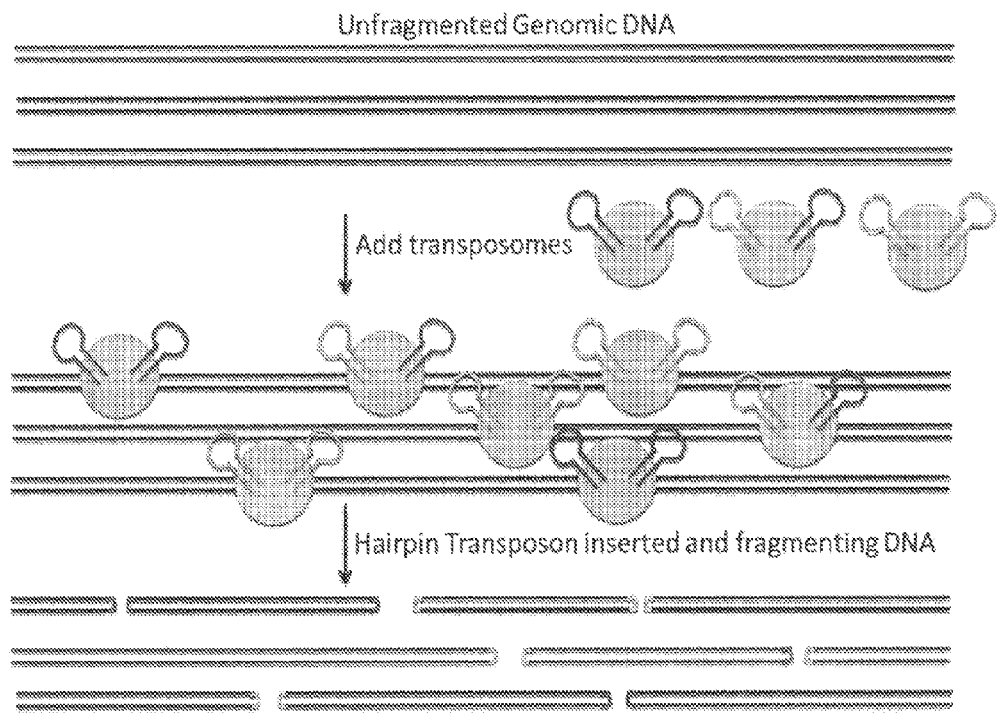
FIG. 5. Simplified schematic illustrating trasposon-based paired-end rolony library construction. Gaps in the libraries will exist following the insertion, but these easily closed and, for clarity, are not illustrated clarity.

Rolony technology involves rolonies (i.e., Rolling circle amplicon cOLONIES). Rolonies are created by rolling circle amplification (RCA) of a circularized DNA fragment (FIG. 1). Rolonies may be sequenced using sequencing-by-synthesis (SBS) (18 bases—FIG. 5) and/or sequencing-by-ligation (SBL, International Patent Application Publication No. WO2011/044437). FIG. 1 shows rolonies randomly immobilized on a glass surface, but rolonies may similarly be sequenced (by SBS and/or SBL) when bound to a patterned silicon surface. Rolonies provide a simple tool that often can eliminate the need for emulsion PCR (ePCR) and thereby provide the option of eliminating an often expensive and labor intensive step in many next generation sequencing methods. Also, rolonies are much smaller than the beads used in ePCR, thus allowing for a much higher density when they are immobilized on a flowcell. One feature of certain embodiments of our platform in the increased density of sequencing information that can be obtained using, for example, rolony technology.

Paired-end reads are very useful for genome assembly and read mapping. For example, structural polymorphisms can be difficult to identify without paired-end reads. In certain embodiments, our platform involves a paired-end sequencing strategy for rolonies that permits haplotype resolved identification of polymorphisms.

In certain embodiments, our platform involves an ISFET DNA sequencing device with a submicron pitch. Our platform can allow a density of $10^9$ sensors in little more than 1 inch$^2$. Such an ISFET DNA sequencing device is described in detail below. This represents an increase in the density of sensors of up to two orders of magnitude compared to, for example, ION 318 chips (Ion Torrent Systems, Inc., South San Francisco, Calif.).

In some embodiments, our platform can involve sequencing from rolonies using sequencing-by-synthesis (SBS) and/or sequencing-by-ligation (SBL). Typically, SBS is performed on a DNA fragment that has been immobilized on, for example, a surface or a bead. SBS is typically performed in a single direction because SBS requires a polymerase which operates in the 5'→3' direction. We have modified typical SBS sequencing by preparing rolonies from a paired-end genomic library. Once circularized into rolonies, both strands can be sequenced in the 5'→3', thereby at least doubling the sequencing information that may be obtained in a single read.

Our platform may be used in conjunction with SBS sequencing that employs any suitable dNTPs. For example, our platform can support SBS using natural dNTPs and/or dNTPs that possess any form of detectable label. Our platform is also compatible with SBS protocols that involve reversible terminators.

Figure 3:
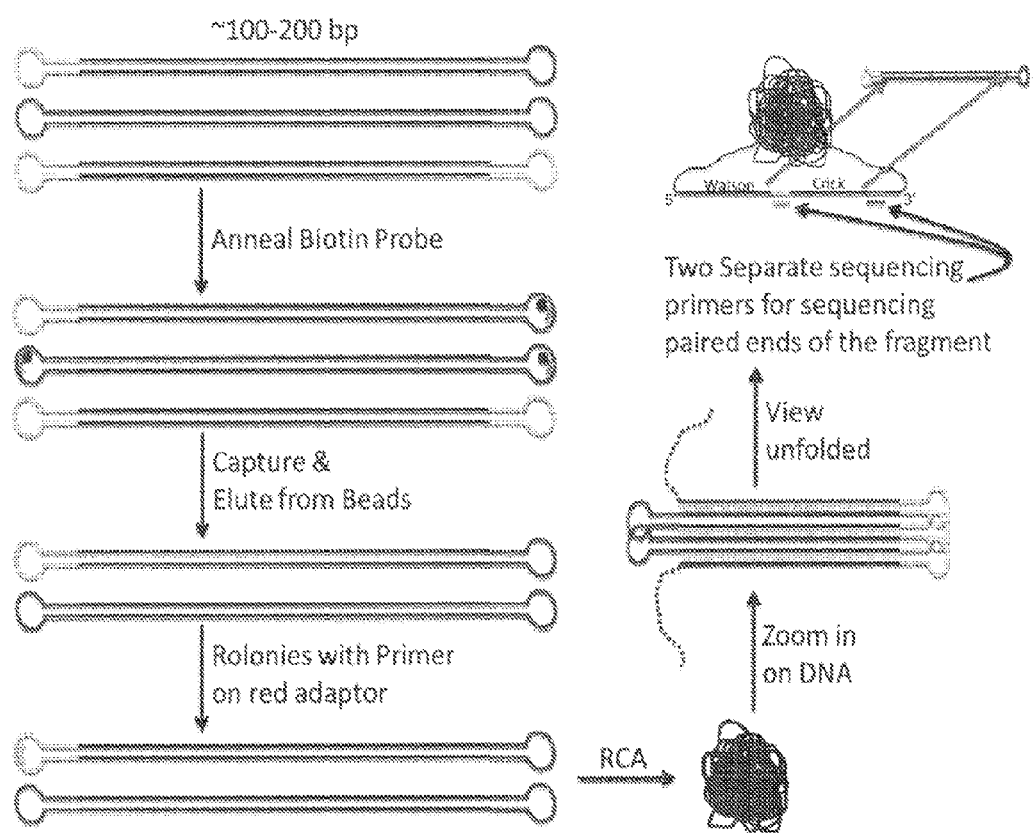
FIG. 3. Paired-end rolony sequencing. If a standard fragment library is constructed with the adaptor sequences being hairpins, the rolony will contain a concatamer of the Watson and Crick strands.

A double stranded DNA library can be directly converted into a circularized library by ligating hairpin primers to the fragment (FIG. 3). In some alternative embodiments, the hairpin-circularized fragment library can be generated using Tn5 transposase (FIG. 5; Adey et al. 2010 Genome biology 11:R119). Regardless of how the hairpin-circularized fragment library is generated, the fragments can be amplified by rolling circle amplification (RCA) to form rolonies that contain concatamers of the Watson and Crick strands (FIG. 3). Therefore, both stands can be sequenced in 5'→3' direction using a polymerase. There may be, however, secondary structure in the rolonies because both strands are present (FIG. 3). To sequence these rolonies, one may use a polymerase with strand displacement activity.

One can construct paired-end rolony libraries as shown in FIG. 3. We have sequenced two bases in each direction on paired-end rolonies using fluorescent SBS reagents (e.g., from Intelligent Bio-Systems, Inc., Waltham, Mass.). To perform paired-end sequencing, the rolonies were immobilized on a positively charged surface, and an anchor primer was annealed to one of the primer sites. Two bases were sequenced using standard SBS methods (Guo et al. 2010 Acc Chem Res 43:551-563; Guo et al. 2008 Proc Natl Acad Sci USA 105:9145-9150; Bi et al. 2006 J Am Chem Soc 128: 2542-2543). After two bases were sequenced, we stripped the anchor primer using 65% formamide at 50° C. Next, we annealed an anchor primer to the other primer site and sequenced two bases from the other strand i.e., the paired-end. The paired-end rolonies were brighter than standard rolonies, and without wishing to be bound by any particular theory, the brighter signal may be due to secondary structure maintaining the rolonies' compact nature.

Figure 4:
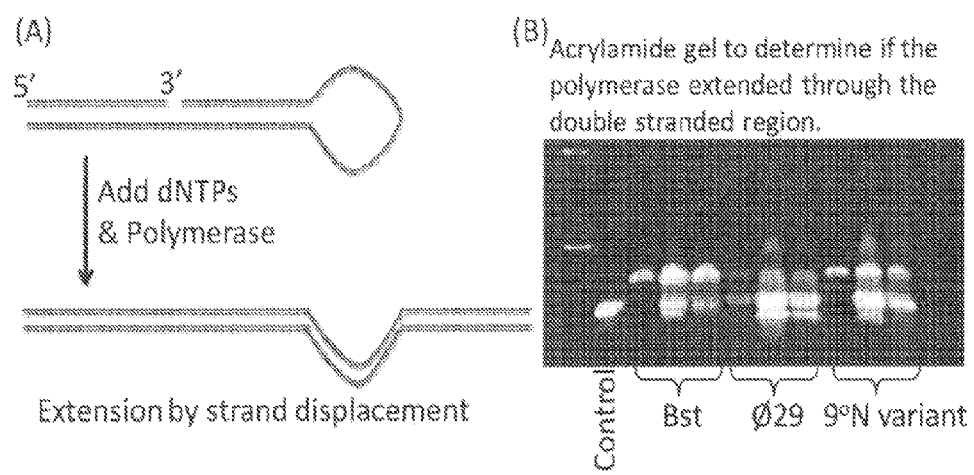
FIG. 4. Strand displacement test. (A) A hairpin oligo was synthesized and an anchor primer was used that aligns to an extension on the hairpin oligo leaving a nick (no gap) as pictured above. Various polymerases were used to determine if extension through the double stranded region was possible via strand displacement. (B) Three different polymerases (Bst, $\phi$29, 9° N variant) were tested for with different concentrations test oligo and anchor primer. Lane 1 and Lane 12 are 25 bp DNA ladder. Lane 2 is the control, which is incubated without polymerase. The three tested polymerases are shown as labeled on the figure. The first lane of each set is 10 µM of the hairpin oligo. The second and third lanes are 100 µM hairpin oligo, but the second lane has 2× loading relative to the third lane. This test shows that all enzymes have strand displacement activity.

As noted above, to sequence certain rolonies one may benefit from using a polymerase with strand displacement activity. Exemplary polymerases showing sufficient strand displacement properties for sequencing paired-end rolonies include, for example, Bst DNA Polymerase (New England BioLabs, Inc., Ipswich, Mass.), φ29 DNA Polymerase (New England BioLabs, Inc.), and a 9° N variant DNA Polymerase (THERMINATOR, New England BioLabs, Inc.) (FIG. 4), other 9° N variants, 9N, etc. One can use one or more of these exemplary polymerases in, for example, a paired-end rolony sequencing strategy using fluorescent SBS because it will incorporate the reversible terminator dNTPs. In other embodiments, one or more of these exemplary polymerases may be used in connection with the electrical sequencing strategy described below.

Rolonies are typically sufficiently bright to sequence by SBS and/or SBL using, for example, fluorescence as the means of detection. In many embodiments, 2,000-5,000 copies of the library may be concatamerized in the rolonies. However, in embodiments described in more detail below involving electrical sequencing, more copies of the library may be required. In some of these embodiments, one may have at least 10,000 copies of the library to generate sufficient signal to noise to accurately detect base extensions and sequence DNA.

Figure 6:
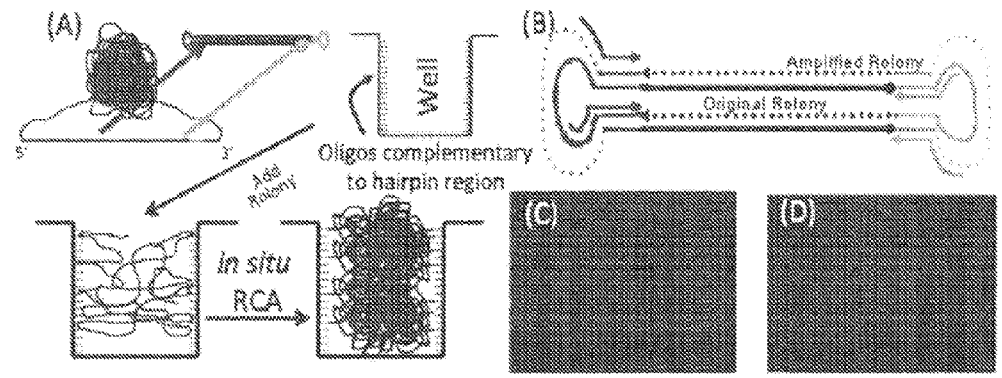
FIG. 6. Rolony Amplification Strategy. (A) The rolony will be immobilized in a sensor well that has amplification primers on the walls. The rolony will be amplified by RCA in situ to generate increased signal. (B) Amplified Rolony Structure shown in circular format. The rolonies are linear concatamers of the circular library and its complement. For simplicity, we show the rolony in circular format. The amplified rolonies contain both the original rolony and the complement. The complement is identical to the original rolony except the hairpins are now complemented. The "Watson" (solid black line 5'→3' in arrow direction) strand from both amplified rolonies can be sequenced using two primers and the same can be done with the "Crick" (dotted black line 5'→3' in arrow direction strands. (C) Unamplified rolonies. (D) Amplified rolonies, generated with primers complementary to the original rolony. The amplification was on a regular slide and all primers were not tethered to the surface, hence the large rolonies.

The rolony signal may be amplified by any suitable method such as, for example, a biochemical method or an electrical method. One exemplary biochemical method for amplifying the rolonies is diagrammed in FIG. 6. One can load standard rolonies into the wells of a silicon sequencing chip (FIG. 6A). The sides of the wells can be functionalized with one or more primers—e.g., two primers: one complementary to the rolony and one the same sequence as the rolony. Adding the DNA polymerase results in amplification of the rolony as shown schematically in FIG. 6B. FIG. 6 also show a comparison of unamplified rolonies (FIG. 6C) and rolonies amplified as shown in FIG. 6A and FIG. 6B (FIG. 6D). Using this strategy one may obtain amplifications of at least 10-fold such, for example, at least 20-fold, at least 30-fold, at least 40-fold, at least 50-fold, at least 60-fold, at least 70-fold, at least 80-fold, at least 90-fold, at least 100-fold, at least 150-fold, at least 200-fold, at least 250-fold, at least 500-fold, or at least 1000-fold. In particular embodiments, one can amplify rolonies at least 100-fold.

Emulsion-based haplotype resolved genome library construction is described generally above with reference to FIG. 10. This emulsion-based library construction method may be modified on one or more ways. For example, one can introduce the Tn5 transposase following the amplification. The Tn5 transposase can be introduced by merging the droplets where the MDA occurred with Tn5-containing droplets. Droplets may be merged by employing ionic surfactants and creating two subsets of droplets: one subset containing the multiple displacement amplified (MDA) genomic fragment and a first ionic surfactant, and a second subset containing the Tn5 transposase and an ionic surfactant having a charge opposite of that possessed by the first ionic surfactant. For example, one can perform the MDA in droplets with an anionic surfactant. Then, one can preload droplets with a cationic surfactant with Tn5. Following amplification, the droplets can be mixed so that droplets carrying opposite charges can merge.

While MDA of small DNA quantities can lead to random amplification of the random hexamers, this effect can be diminished by using hexamers containing nitroindole bases at the 5' end. Additionally, one can include trehalose in the buffer to reduce primer self-amplification. We have tried both approaches and we have been able to eliminate random amplification, as measured by no amplification in the negative controls.

Emulsions may be prepared using standard techniques. For example, one exemplary approach for making the emulsions is by bulk methods, where the emulsion is made by a TissueLyser (Qiagen; Valencia, Calif.) or homogenizer. Bulk emulsions are easy to make, but droplet size can be variable. Alternatively, one can use a microfluidic device to generate droplets. One feature of using a microfluidic device is that the droplets are monodispersed—i.e., of similar or even identical size. In some embodiments, one can merge the aqueous phase MDA components in the microfluidic device immediately before forming droplets to prevent amplification before emulsification. Also, within the microfluidic device, one can merge a Tn5-containing droplet with the amplified sample directly on the device.

Assembly of the 100 kb-200 kb fragment may be accomplished by any suitable method. Exemplary methods include, for example, de novo assembly and assembly by mapping reads. In some 96-well-based embodiments, assembly may be performed by mapping reads. For emulsion-based embodiments, since only a single molecule is be present per droplet, one can perform de novo assembly of the individual 100 kb-200 kb fragments using conventional de novo assembly tools (Zhang et al. 2011 *PLoS ONE* 6:e17915; Chaisson et al. 2009 *Genome Research* 19:336-346; Lin et al. 2011 *Bioinformatics* 27:2031-2037; Chaisson and Pevzner, 2008 *Genome Research* 18:324-330). Alternatively, one can perform the subassembly by mapping the reads.

The second phase of the assembly involves assembling the 100-200 kb fragments into the entire genome. These reads can be assembled while retaining haplotype information. To assemble the 100-200 kb fragments, one can map these to the reference genome and use the polymorphisms to guide the full genome assembly.

To ensure that our approach resolves haplotypes, one can sequence a sample for which the haplotypes are known. Additionally, one can validate a select number of haplotypes over large distances using the approach developed by Dapprich et al. (2008 *Nucleic Acids Research* 36:e94).

In some embodiments, our platform may be used in conjunction with DG-ISFET technology. As used herein DG-ISFET refers to ion sensitive field effect transistors (ISFETs) that include a double gate. The second gate, with the floating gate being the first gate, can function as an access transistor for the ISFET device, thereby decreasing the size of an individual device footprint. Such a reduced footprint size can allow arrays with more ISFETS per area. Also disclosed here are methods of monitoring analytes in a target material that can offer lower detection limits thereby allowing for detection in smaller sample sizes.

ISFET devices are impedance transformation devices that operate in a manner similar to that of a metal oxide semiconductor field effect transistor (MOSFET), and are particularly configured to selectively measure ion activity in a solution (for example, hydrogen ions in a solution).

Figure 15:
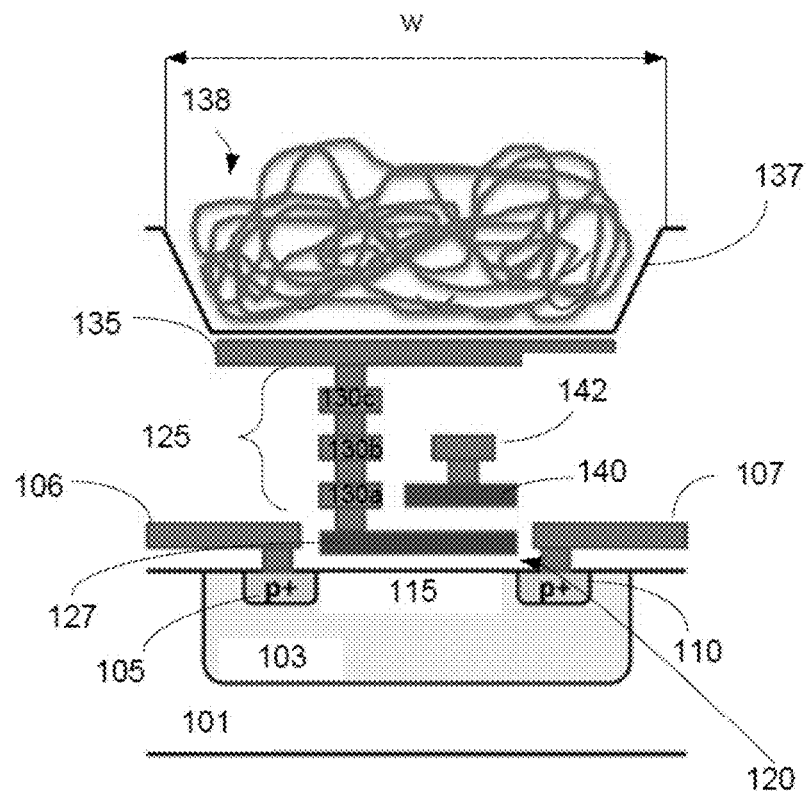
FIG. 15 depicts a cross sectional view of an exemplary ion-sensitive field effect transistor (ISFET) device disclosed herein.

FIG. 15 depicts a cross sectional view of an exemplary ion-sensitive field effect transistor (ISFET) device 100. Devices such as that depicted in FIG. 15 can be fabricated using conventional CMOS (complementary metal oxide semiconductor) processes, for example. Assuming a CMOS fabrication, the device can include a substrate 101, for example a p-type silicon substrate. An n-type well 103 is formed into the substrate to form the body of the device. Highly doped p-type regions form a source 105 and a drain 110. Metal contacts 106 and 107 are formed to provide electrical connection to the source and the drain. A channel region 115 is located between the source and the drain within the body of the substrate. A first insulating layer 120 is formed over the channel region. The first insulating layer can be formed of an oxide for example. The first insulating layer can also be referred to as the gate oxide, because as indicated below it is between the first floating gate and the body (i.e., substrate) of the device. The first insulating layer 120 can, but need not be, part of a larger structure. For example, in the device depicted in FIG. 15, the "white" space between the metal contacts and the ion sensitive membrane can generally be made of an insulating material. The first insulating layer 120 can, but need not be, a portion of that larger area of that insulating material.

A first floating gate 127 is formed over the first insulating layer. The first floating gate includes a polysilicon gate formed directly over the first insulating layer. The first floating gate can be coupled to multiple metal layers 130*a*, 130*b*, and 130*c* disposed within an oxide layer, which can collectively be referred to as the first floating gate structure 125. The first floating gate, and the first floating gate structure are configured to create or initiate or utilize the ion sensitive field effect. The first floating gate structure, and the first floating gate are referred to as "floating" because they are electrically isolated from other conductors associated with the ISFET. The first floating gate structure is disposed between the first insulating layer and the ion sensitive membrane 135. Analytes in a target material 138 in contact with the ion-sensitive membrane, particularly right above the floating gate structure, alters the electrical characteristics of the device, causing a current to flow through the channel region between the source and the drain.

Disclosed devices can also include a second gate 140. The second gate 140 is formed over the first floating gate 127, but not in electrical connection with the first floating gate 127. The second gate can be capacatively coupled to the first gate. The second gate 140 can be connected, via an access contact 142 to a control voltage, $V_{CTRL}$. The voltage of $V_{CTRL}$ affects the functioning of the first floating gate 127. For example, if $V_{CTRL}$ is set to an "on" voltage, current is able to flow in the channel region between the source and the drain. If $V_{CTRL}$ is set to an "off" voltage, current is not able to flow in the channel region between the source and the drain. In this way, the second gate 140 can act as an access transistor for the ISFET. By controlling the voltage on the second gate, the ISFET can either be read from, or not. In some embodiments, an on voltage can be about 0 V. In some embodiments, when $V_{CTRL}$ is greater than about 0 V, less current flows through the channel region between the source and the drain than when $V_{CTRL}$ is about 0 V. In some embodiments, when $V_{CTRL}$ is about 5 V or greater, current cannot flow through the channel region between the source and the drain.

Figure 16:
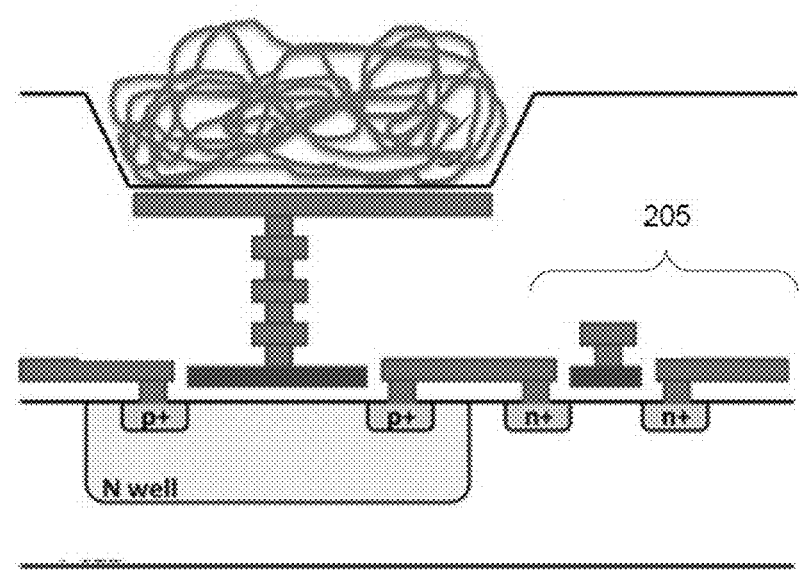
FIG. 16 depicts a cross sectional view of an ISFET device of the prior art.
Figure 17:
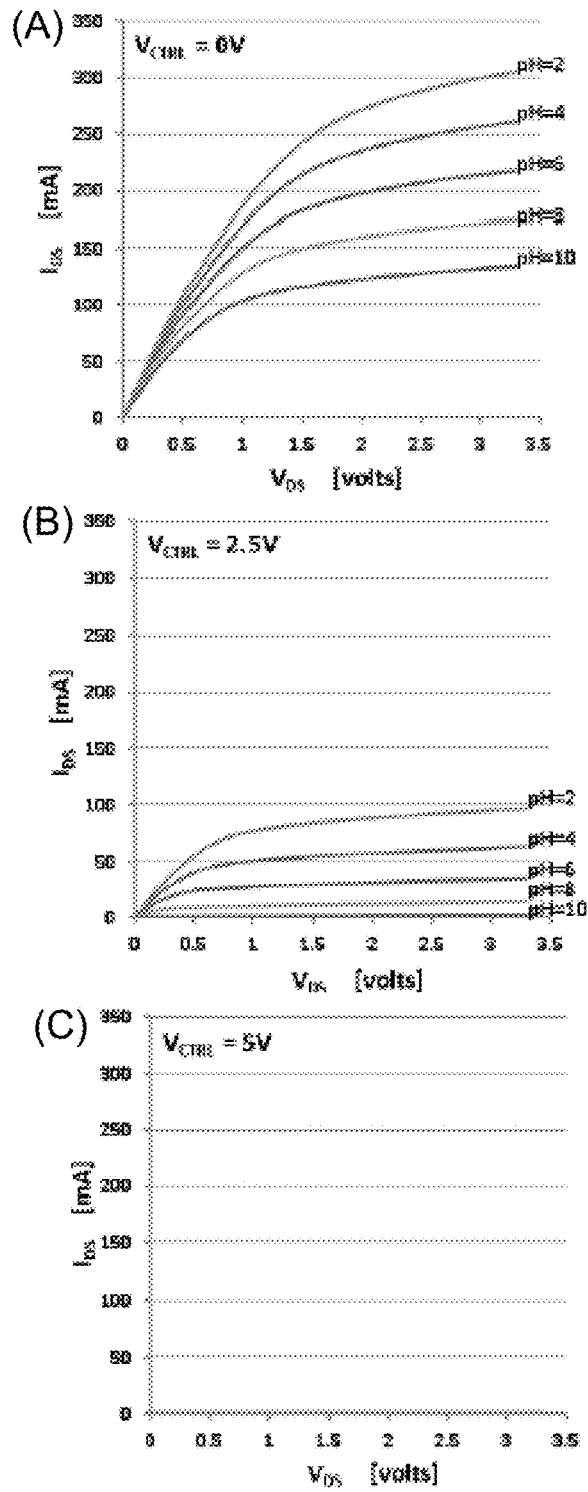
FIGS. 17A through 17C show simulation results of current ($I_{DS}$) versus potential on the source and/or drain ($Y_{DS}$) for disclosed devices at different $V_{CTRL}$.

FIG. 16 depicts a prior art ISFET device. Components similar to those discussed above are not specifically enumerated or labeled herein. ISFET devices of the prior art, such as that depicted in FIG. 16 would generally be fabricated in electrical connection with a separate access transistor 205. The access transistor in this prior art device functions to allow the ISFET device to be read, i.e., it allows it to carry a current and therefore detect the presence of the analyte in the target material. As seen in the device depicted in FIG. 16, the prior art device, because of the necessity of being configured with the separate access transistor, has a larger sensor area than that of devices disclosed herein. In contrast to the depicted prior art device, disclosed devices do not need a separate access transistor.

Disclosed devices can be configured with a well. The device depicted in FIG. 15 includes a well 137. A well can generally be positioned over the first floating gate structure 125 and over the ion sensitive membrane 135. Such a configuration allows ions in the well to pass through the ion sensitive membrane and act on the first floating gate structure and ultimately the first floating gate, thereby allowing (assuming that $V_{CTRL}$ is set to an on value) current to flow between the source and the drain. The amount of current flowing between the source and the drain is indicative of the amount of ions (for example hydrogen ions) in the target material in the well. The well can generally have any configuration that can house or contain at least some volume of target material.

Devices disclosed herein can be fabricated or utilized in an array format. Disclosed devices, because they do not necessarily have to include a separate access transistor, may have advantages over previously utilized devices because a single device can have a smaller area. This can be advantageous when the devices are being formed in an array of devices, because smaller devices can allow more devices to be packed into the same overall space. A disclosed array can include a plurality of devices. Any convenient number of devices can be included in an array. In some embodiments, an array can include $10^3$ (thousands) of devices, $10^6$ (millions "M" of devices), or $10^9$ (billions "B" of devices). In some embodiments, an array can include $10^6$ or even $10^9$ devices in an area that is on the order of a square inch. Disclosed arrays can be two dimensional or three dimensional arrays.

In some embodiments, a well and the associated device can be scalable, meaning the size can be decreased as afforded by processing techniques. The size of a device can be characterized by the size of the well. In some embodiments, the well can be characterized by the width of the well. The width of the well 137 in FIG. 15 is given by the dimension w. In some embodiments, the width of a well can be less than 5 micrometers (μm). In some embodiments, the width of a well can be less than 4 μm. In some embodiments, the width of a well can be less than 3 μm. In some embodiments, the width of a well can be a few μm or less. In some embodiments, the width of a well can be about 1 μm or even less than 1 μm.

Disclosed devices can also include other additional components not discussed herein. Examples of such other components can include, for example a reference electrode, and various other electronic components. Alternatively or additionally, disclosed devices can include readout circuits (other than or in addition to those discussed herein), and power management components for example.

The above discussed components of disclosed devices can be fabricated using techniques and materials known to those of skill in the art. In some embodiments, silicon-on-insulator (SOI), or silicon-on-sapphire (SOS) technology can be utilized. As examples of fabrication methods and steps that can be utilized herein, in some embodiments, a standard 90 nm CMOS process by Taiwan Semiconductor Manufacturing Corporation (TSMC) through MOSIS can be utilized. The second gate can be constructed by the second poly step offered in double poly CMOS processes. Similarly, in some embodiments, the second gate can be constructed by the first metal (M1) layer in standard CMOS processes. Generally, components of the device can be fabricated from materials commonly utilized for such components. In some embodiments, the second gate can be made of the same materials that the first floating gate is made of, for example, polysilicon. In some embodiments, ion sensitive membranes can be fabricated from a metal oxide, or nitride. In some embodiments, the ion sensitive membrane can be fabricated from $Ta_2O_5$, $SiO_2$, $Al_2O_3$, $HfO_2$, $TiO_2$, or $Si_3N_4$. In some embodiments, the ion sensitive membrane can be fabricated from $Ta_2O_5$.

Disclosed arrays can also be configured along with various methods and/or electronics for monitoring the current flowing through the channel region of each device, or more specifically, for example for reading the pH values of each well. Readout speed can be problematic in such arrays. The nucleotide incorporation transient normally takes place within about 5 seconds. It can therefore be important to capture enough data form all sensors (in the case of a $10^9$ array, all $10^9$ sensors) in about 5 seconds. In a $10^9$ array, that implies that the unit cell readout time is only 50 picoseconds (ps). In some embodiments, disclosed arrays can therefore be implemented with multiple or a plurality of parallel readout circuits. In some embodiments, a $10^9$ array can be implemented with at least 20 parallel readout circuits. In some embodiments, a $10^9$ array can be implemented with at least 40 parallel readout circuits. In some embodiments, a $10^9$ array can be implemented with 50 parallel readout circuits. In an exemplary $10^9$ array including 50 parallel readout circuits, the unit cell readout time would be about 2.5 nanoseconds (ns).

Disclosed devices can measure various analytes in a target material. Various analytes other than, or in addition to those discussed herein, can be sensed by selecting appropriate materials for the ion sensitive material. For example, ammonium can be detected, using for example aniline trimmers. In some embodiments, ionic analytes can be measured. In some embodiments, ionic analytes of interest can include, for example hydrogen ions or protons ($H^+$). Concentration of protons in a solution is often referred to by the pH, which is the −log of the hydrogen ion concentration. In embodiments where the analyte of interest is hydrogen ions, exemplary devices can function to detect relatively small amounts of hydrogen ions, for example on the order of $10^4$ hydrogen ions.

Also disclosed herein are methods of determining the concentration of an analyte in a target material. Disclosed methods can include use of or providing a disclosed device. A step of providing a device can include fabricating a device, procuring a device (whether via sale or otherwise), obtaining a device, or configuring a device to use it in a disclosed method. Disclosed methods can also include a step of applying an "on" potential, or $V_{CTRL}$ of "on" to the second gate. As discussed above, when $V_{CTRL}$ is on, current is allowed to flow, in response to hydrogen ions (in such an example) in the target material in the well, between the source and the drain. If $V_{CTRL}$ is set to "off", current is no longer allowed to flow between the source and the drain. Disclosed methods can include additional, optional steps of applying a potential of greater than 0 V, or a $V_{CTRL}$ off voltage at some time after the $V_{CTRL}$ on was applied. Application of a $V_{CTRL}$ off will stop the current flowing through the channel region between the source and the drain.

Disclosed methods can also include a step of monitoring the current flowing through the channel region between the source and the drain. The amount of current flowing through the channel region can vary depending on the amount of analyte (hydrogen ions in such an example) in the target material. The amount of current can be monitored using known electronic components and/or mathematical methods.

Disclosed methods can also include a step of determining the concentration of the analyte in the target material based on the monitored current. In some embodiments, the current can increase as the amount of the analyte increases. In some embodiments where the analyte of interest is hydrogen ions, an increase amount of hydrogen ions (which would be a lower pH) can cause more current to flow through the channel region between the source and the drain. The concentration of the analyte in the target material can be determined, based on the monitored current using known electronic components and/or mathematical methods. Disclosed methods can also optionally include the additional step of converting the concentration of the analyte in the target material into a pH measurement. The concentration of the analyte in the target material can be converted into a pH measurement using known electrical components and/or mathematical methods.

Generally, disclosed devices also have a potential applied to the source and/or drain. Such potential(s) can be referred to as $V_{DS}$. $V_{DS}$ can also function to control the amount of current flowing through the channel region between the source and the drain in response to the concentration of the analyte in the target material. As $V_{DS}$ is increased, the amount of current flowing through the channel region in response to a given concentration of analyte in a target material is increased. Stated another way, at a constant analyte concentration, increasing the $V_{DS}$ will increase the current flowing through the channel region between the source and the drain.

It is thought, but not relied upon that use of relatively high $V_{DS}$ may allow the device to function in "avalanche" mode. A device functioning in avalanche mode can allow the signal to be amplified. This could allow disclosed devices to detect smaller amounts of analytes in the target material. Avalanche mode allows a signal caused by a proton(s) interacting with the ion sensitive material to be amplified. More specifically, avalanche buildup and impact ionization phenomena can be used to amplify the detected signal inside the channel region of the device. When VDS is set to the point of avalanche breakdown, the large electric field in the channel region of the device can cause a single electron (or hole) to have enough energy to generate another electron-hole pair by impact ionization. These events can then continue until the current is amplified to an extent that it can be monitored, as discussed above. In some embodiments, $V_{DS}$ can be set to at least about 5 V in order to cause the device to operate in avalanche mode. In some embodiments, $V_{DS}$ can be set to at least about 6 V in order to cause the device to operate in avalanche mode.

In some embodiments, once the current through the channel region is detected, the potential applied to the source and the drain can be reduced. Reducing the potential on the source and the drain can serve to quench the avalanche mode. This can allow the device to be prepared for another cycle of monitoring the current.

Disclosed embodiments of the method that utilize the relatively high $V_{DS}$ in order to allow the device to function in avalanche mode can be advantageous because they should have a lower signal to noise ratio because the amplification takes place at the sensor itself. Furthermore, because no additional or modified structures are necessary in the device itself, the method can be utilized with any ion sensitive field effect transistor. In some embodiments, methods that utilize relatively high $V_{DS}$ in order to allow the device to function in avalanche mode can be utilized in combination with disclosed devices that include a second gate. Such a combination would afford an array that can include $10^9$ devices having very small dimensions but would still afford a method of detection for very limited sample sizes.

Figure 11:
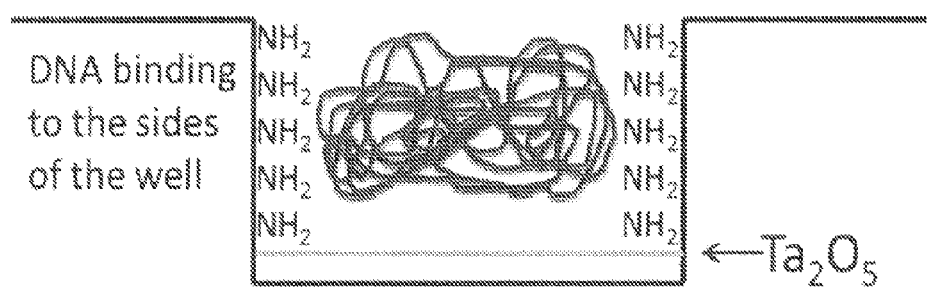
FIG. 11. Schematic of a unit cell. (a) DNA binding to the sensor well. We will either use the $NH_2$ groups to bind the rolonies or attach oligos to the $NH_2$ groups that will be used for amplification if needed (FIG. 6).

One can functionalize the inner walls of the device with $NH_2$ groups for DNA binding (FIG. 11). If no amplification of the rolony is needed, one can use these sites to directly bind rolony. However, if amplification is needed, one can bind the primers (one or more for hyperbranched amplification) to these groups. FIG. 11 also shows the sensor/well coated with a tantalum oxide ($Ta_2O_5$) layer for proton sensitivity. Other metal oxides can be used for the proton sensing gate, including, for example, $SiO_2$, $Si_3N_4$, $Al_2O_3$, $HfO_2$, and $TiO_2$.

The sensitivity of the ISFET array is involved in the design of sequencing integrated circuits. In some embodiments, the sensitivity may be increased. In some cases, the sensitivity may be increased using a biochemical amplification, as described above, for amplifying the amount of DNA per sensor/well. In other cases, the sensitivity of ISFETs can be further increased by operating in "avalanche mode." One can use avalanche buildup and impact ionizations phenomena to amplify the detected signal inside the ISFET channel, similar to the structure of the avalanche photodetector (APD) for single photon detection. FIG. 14 shows a schematic illustration of an avalanche ISFET (A-ISFET), which has structure similar to an ISFET except that the applied voltage is increased to the point of avalanche breakdown. Due to the large electric field in the channel of A-ISFET, a single electron (or hole) can get enough energy to generate another electron-hole pair by impact ionizations. These events continue until the readout circuit detects the amplified current. Then the bias voltage ($V_{DS}$) is reduced to prepare the A-ISFET for another readout cycle. Since the amplification occurs at the sensor itself, this amplification strategy can increase the system signal to noise ratio. In addition, the physical structure of the A-ISFET can be made identical to a conventional ISFET. Therefore, it can be easily implemented into any ISFET structure (e.g. DG-ISFET), without any area overhead.

Figure 12:
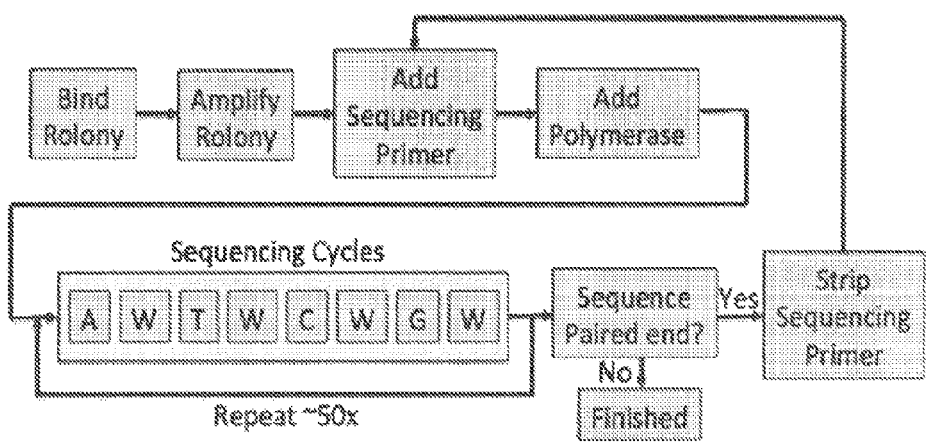
FIG. 12. Sequencing workflow. In the sequencing cycles, W stands for wash.

The sequencing workflow for ISFET-based embodiments is illustrated in FIG. 12. One can select buffer to reduce interference with the protons released during the sequencing. The buffer can be designed to have an absolute minimum amount of buffering capacity, hence allowing a maximum number of liberated protons to interact with the metal oxide gate coating.

The transient pH readings can be converted to the base call. Homopolymer repeats may create a base calling challenge because one, two, three, or more bases of the same identity in a row can be challenging to differentiate. One can, however, call the number of bases in a homopolymer run by the intensity of the signal. One can design the sequencing primers so that a control region containing each of the four bases is encountered in the first cycle of the base flows. This can allow calibration of the signal. One can, alternatively, call the bases by using a mathematical model that factors in the possibility of lead and lag signal. Read lengths that exceed 50-100 bases may require a sophisticated model of the base incorporation. Exemplary mathematical models include, for example, the publicly available algorithm developed by Solexa and available at www.ebi.ac.uk/goldman-srv/AYB/.

In the preceding description, reference is made to the accompanying set of drawings that form a part of this specification and in which are shown by way of illustration several specific embodiments. It is to be understood that other embodiments are contemplated and may be made without departing from the scope or spirit of the present disclosure. The precedinging detailed description, therefore, is not to be taken in a limiting sense.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

In the preceding description, the term "and/or" means one or all of the listed elements or a combination of any two or more of the listed elements; unless otherwise specified, "a," "an," "the," and "at least one" are used interchangeably and mean one or more than one; the recitations of numerical ranges by endpoints include all numbers subsumed within that range (e.g., 1 to 5 includes 1, 1.5, 2, 2.75, 3, 3.80, 4, 5, etc.); and the terms "comprises" and variations thereof do not have a limiting meaning where these terms appear in the description and claims.

The present invention is illustrated by the following examples. It is to be understood that the particular examples, materials, amounts, and procedures are to be interpreted broadly in accordance with the scope and spirit of the invention as set forth herein.

EXAMPLES

Example 1

High molecular weight DNA was purified from whole blood using the Gentra Puregene Blood Kit (Qiagen; Valencia, Calif.) per manufacturer protocol. DNA concentration was then determined using the nanodrop (Thermo Scientific; Waltham, Mass.). Whole genome amplification was then carried out using REPLI-g Mini Kit (Qiagen; Valencia, Calif.). Using this kit 300 ng of DNA was placed in the D1 buffer of 3 minutes at room temperature. After this incubation an equal amount of N1 was added. The denatured DNA was then diluted in water and 0.6 pg (approximately 10% of the human genome) of DNA was added to Repli-G reaction buffer and Repli-G DNA Polymerase. The reaction was carried out at 30° C. for 18 hours, followed by 3 minutes at 65° C. to denature the enzyme. The amplified DNA was then purified by completing a phenol:chloroform:isoamyl alcohol purification and 100% ethanol precipitation and resuspended in 50 µl low TE. DNA concentration was determined using the Qubit® 2.0 Fluorometer (Invitrogen; Grand Island, N.Y.). In addition, to the diluted sample a negative control (no DNA) was run to ensure that the amplification products were not an artifact of the reaction. Using this protocol we have yet to see any amplification in our negative control reactions.

To carry out whole genome resequencing, a library was produced from isolated DNA using the Ion Xpress™ Fragment Library Kit (Life Technologies; Grand Island, N.Y.) per manufacture protocol. Briefly, DNA was fragmented using the Ion Shear™ Reagents incubating at 37° C. for 30 minutes. The fragmented DNA was then purified using the Agencourt® AMPure® XP Kit (Beckman Coulter; Brea, Calif.). The fragmented DNA was eluted with 50 µl RNase free water. After purification, adaptors were ligated to the fragmented DNA. The ligation product was purified using the Agencourt® AMPure® XP Kit. The purified DNA was then run on a 6% polyacrylamide gel; the ligation was then size selected and excised from the gel and eluted in PAGE elution buffer at 50° C. overnight. The library was then purified by completing a phenol: chloroform:isoamyl alcohol purification and 100% ethanol precipitation and resuspended in 50 µl low TE. The purified and size selected DNA was then PCR amplified. The final library was purified using the Agencourt® AMPure®XP Reagent. Final library DNA was eluted in 20 µl Low TE and stored at −20° C. DNA concentration was determined using the Qubit® 2.0 Fluorometer. Whole genome resequencing data was analyzed using CLC Genomic Workbench 5.1 sequence reads were mapped back to the hg19 genome reference sequence. We have used this method to sequence human DNA.

Example 2

DG-ISFET Simulation

The functioning of a device, such as that disclosed in FIG. 15 was simulated using a SPICE (Simulation Program with Integrated Circuit Emphasis) simulation. The device was assumed to be as depicted in FIG. 15 made from a 0.35 µm CMOS process from Taiwan Semiconductor Manufacturing Corporation (TSMC). The results of the simulation are shown in FIGS. 3A through 3C. As seen there, the highest sensitivity to protons is achieved when $V_{CTRL}$ is grounded. The sensor becomes disabled ($V_{CTRL}$ is set to "off") when $V_{CTRL}$ is at 5 V.

Prototype

A prototype $10^6$ array containing (1000×1000) devices, such as that disclosed in FIG. 15 (scalable to $10^9$) will be fabricated using 0.35 TSMC double poly CMOS processing through MOSIS. It will include wells having a width of 0.5 µm and a 0.8 µm center to center pitch. The wells will be coated with a tantalum oxide ($Ta_2O_5$) layer for proton sensitivity. In order to perform the readout of the complete array in a desirable time, a multi-channel readout technique will be used, where each channel will be responsible for a certain portion of the sensor data. The readout process will be similar to image data readout in a regular digital camera.

Thus, embodiments of double gate ion sensitive field effect transistors are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for preparing a DNA molecule for sequencing, the method comprising:
fragmenting the DNA molecule into double-stranded fragments;
amplifying at least a portion of the double-stranded fragments;
preparing an emulsion that comprises a first subset of droplets and a second subset of droplets, wherein:
the first subset of droplets comprises amplified DNA fragments; and
the second subset of droplets comprises a plurality of transposons selected to insert into the amplified DNA fragments and comprising loops that, when the transposon inserts into a fragment, circularizes the fragment;
circularizing the fragments so that the first end of a fragment comprises a first loop connecting the strands of the fragment and the second end of the fragment comprises a second loop connecting the strands of the fragment;

annealing a first sequencing primer to the first loop oriented to sequence at least a portion of one strand of at least one fragment; and annealing a second sequencing primer to the second loop oriented to sequence at least a portion of the other strand of the fragment.

2. A method for sequencing a DNA molecule, the method comprising:

fragmenting the DNA molecule into double-stranded fragments;

amplifying at least a portion of the double-stranded fragments;

preparing an emulsion that comprises a first subset of droplets and a second subset of droplets, wherein:
the first subset of droplets comprises amplified DNA fragments; and
the second subset of droplets comprises a plurality of transposons selected to insert into the amplified DNA fragments and comprising loops that, when the transposon inserts into a fragment, circularizes the fragment;

circularizing the fragments so that the first end of a fragment comprises a first loop connecting the strands of the fragment and the second end of the fragment comprises a second loop connecting the strands of the fragment; and sequencing at least one of the DNA strands.

3. The method of claim 2 wherein sequencing at least one of the strands comprises sequencing-by-synthesis or sequencing-by-ligation.

4. The method of claim 3 wherein sequencing at least one of the DNA strands comprises:

annealing a first sequencing primer to the first loop oriented to sequence at least a portion of one strand of the fragment;

annealing a second sequencing primer to the second loop oriented to sequence at least a portion of the other strand of the fragment; and performing sequencing-by-synthesis.

5. The method of claim 2 wherein:

sequencing at least one of the DNA strands comprises generating a read; and the method further comprises assembling a plurality of reads to generate the sequence of the DNA molecule.

6. The method of claim 2 further comprising preparing an emulsion comprising a plurality of droplets that contain the circularized DNA fragments.

7. The method of claim 2 wherein at least a portion of the DNA fragments are amplified prior to being circularized.

8. The method of claim 2 wherein droplets in the first subset of droplets comprise an electrical charge and droplets in the second subset of droplets comprise an electrical charge opposite of the electrical charge of the droplets in the first subset of droplets.

9. The method of claim 8 wherein circularizing the fragments comprises merging at least one droplet from the first subset of droplets and at least one droplet from the second subset of droplets.

10. The method of claim 2 further comprising immobilizing at least a portion of the circularized DNA fragments to a substrate.

11. The method of claim 10 wherein the substrate comprises a multi-well array.

12. The method of claim 11 further comprising detecting light signals that correspond to nucleotide bases in the DNA sequence.

13. The method of claim 10 wherein the substrate comprises a DG-ISFET device.

14. The method of claim 13 further comprising detecting transient pH readings that correspond to nucleotide bases in the DNA sequence.

15. The method of claim 2 wherein fragmenting the DNA molecule comprises shearing the DNA molecule.

16. The method of claim 2 wherein fragmenting the DNA molecule and circularizing the fragments are performed in a single step that comprises inserting a plurality of transposons into the DNA molecule, wherein transposons insert loops onto the ends of DNA fragments that are generated by inserting the plurality of transposons into the DNA molecule, thereby circularizing the fragments.

17. The method of claim 1 further comprising preparing an emulsion comprising a plurality of droplets that contain the circularized DNA fragments.

18. The method of claim 1 wherein at least a portion of the DNA fragments are amplified prior to being circularized.

19. The method of claim 1 wherein droplets in the first subset of droplets comprise an electrical charge and droplets in the second subset of droplets comprise an electrical charge opposite of the electrical charge of the droplets in the first subset of droplets.

20. The method of claim 19 wherein circularizing the fragments comprises merging at least one droplet from the first subset of droplets and at least one droplet from the second subset of droplets.

21. The method of claim 1 further comprising immobilizing at least a portion of the circularized DNA fragments to a substrate.

22. The method of claim 21 wherein the substrate comprises a multi-well array.

23. The method of claim 22 further comprising detecting light signals that correspond to nucleotide bases in the DNA sequence.

24. The method of claim 21 wherein the substrate comprises a DG-ISFET device.

25. The method of claim 13 further comprising detecting transient pH readings that correspond to nucleotide bases in the DNA sequence.

26. The method of claim 1 wherein fragmenting the DNA molecule comprises shearing the DNA molecule.

27. The method of claim 1 wherein fragmenting the DNA molecule and circularizing the fragments are performed in a single step that comprises inserting a plurality of transposons into the DNA molecule, wherein transposons insert loops onto the ends of DNA fragments that are generated by inserting the plurality of transposons into the DNA molecule, thereby circularizing the fragments.

* * * * *

SEQUENCE LISTING

```
<160> NUMBER OF SEQ ID NOS: 10

<210> SEQ ID NO 1
<211> LENGTH: 66
<212> TYPE: DNA
<213> ORGANISM: Homo sapiens

<400> SEQUENCE: 1
ggatggggaa agaaaggcac cagagaagca gagcgaagac gtggaaacca tagagcctta        60
ctaagt                                                                  66

<210> SEQ ID NO 2
<211> LENGTH: 66
<212> TYPE: DNA
<213> ORGANISM: Homo sapiens

<400> SEQUENCE: 2
ggacggggaa agaaaggcac cagagaagca gagcgaagac gtggaaacca tagagcctta        60
ctgagt                                                                  66

<210> SEQ ID NO 3
<211> LENGTH: 48
<212> TYPE: DNA
<213> ORGANISM: Homo sapiens

<400> SEQUENCE: 3
ggacggggaa aagaaaggca ccaggaagaa catagagcct tactgagt                     48

<210> SEQ ID NO 4
<211> LENGTH: 53
<212> TYPE: DNA
<213> ORGANISM: Homo sapiens

<400> SEQUENCE: 4
ggacggggaa agaaaggcgc gaagacgtgg aaaaccatag agccttactg agt               53

<210> SEQ ID NO 5
```

```
<211> LENGTH: 54
<212> TYPE: DNA
<213> ORGANISM: Homo sapiens

<400> SEQUENCE: 5
ggacggggaa agaaaggcac cagagaagca ggagcgaaga cgtggaaacc atag          54

<210> SEQ ID NO 6
<211> LENGTH: 66
<212> TYPE: DNA
<213> ORGANISM: Homo sapiens

<400> SEQUENCE: 6
ggacggggaa agaaaggcac cagagaagca gagcgaagac gtggaaacca tagagcctta    60
ctgagt                                                               66

<210> SEQ ID NO 7
<211> LENGTH: 66
<212> TYPE: DNA
<213> ORGANISM: Homo sapiens

<400> SEQUENCE: 7
ggacggggaa agaaaggcac cagagaagca gagcgaagac gtggaaacca tagagcctta    60
ctgagt                                                               66

<210> SEQ ID NO 8
<211> LENGTH: 66
<212> TYPE: DNA
<213> ORGANISM: Homo sapiens

<400> SEQUENCE: 8
ggacggggaa agaaaggcac cagagaagca gagcgaagac gtggaaacca tagagcctta    60
ctgagt                                                               66

<210> SEQ ID NO 9
<211> LENGTH: 66
<212> TYPE: DNA
<213> ORGANISM: Homo sapiens

<400> SEQUENCE: 9
ggacggggaa agaaaggcac cagagaagca gagcgaagac gtggaaacca tagagcctta    60
ctgagt                                                               66

<210> SEQ ID NO 10
<211> LENGTH: 45
<212> TYPE: DNA
<213> ORGANISM: Homo sapiens

<400> SEQUENCE: 10
agagaagcag agcgaagacg tggaaaccat agagccttac tgagt                    45
```